(12) United States Patent
Fujita et al.

(10) Patent No.: US 7,210,333 B2
(45) Date of Patent: May 1, 2007

(54) HUMIDITY SENSOR AND METHOD OF USING THE HUMIDITY SENSOR

(75) Inventors: Hiroki Fujita, Aichi (JP); Koichi Fujita, Aichi (JP); Satoshi Sugaya, Aichi (JP); Kenji Kato, Aichi (JP); Ryuji Inoue, Gifu (JP); Noboru Ishida, Gifu (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 10/857,495

(22) Filed: Jun. 1, 2004

(65) Prior Publication Data

US 2004/0237646 A1    Dec. 2, 2004

(30) Foreign Application Priority Data

May 30, 2003   (JP)   ............... 2003-155014

(51) Int. Cl.
*G01N 7/00* (2006.01)
(52) U.S. Cl. .................................... 73/29.05
(58) Field of Classification Search ............ 73/29.05
See application file for complete search history.

(56) References Cited

U.S. PATENT DOCUMENTS

| | | | | |
|---|---|---|---|---|
| 3,161,056 A | * | 12/1964 | Faus | .............. 73/335.05 |
| 3,369,880 A | * | 2/1968 | Mochel | ............... 65/30.1 |
| 4,245,506 A | * | 1/1981 | Meiklejohn | ........ 73/335.03 |
| 4,326,414 A | * | 4/1982 | Terada et al. | ...... 73/335.05 |
| 4,481,813 A | * | 11/1984 | Tanei et al. | ........ 73/335.02 |
| 4,500,940 A | * | 2/1985 | Kuisma et al. | ........ 361/286 |
| 4,656,455 A | * | 4/1987 | Tanino et al. | .......... 338/35 |
| 4,752,855 A | * | 6/1988 | Fedter et al. | .......... 361/286 |
| 4,797,605 A | * | 1/1989 | Palanisamy | .......... 324/689 |
| 4,801,211 A | | 1/1989 | Yagi et al. | |
| 4,938,928 A | * | 7/1990 | Koda et al. | ............ 422/98 |
| 4,970,122 A | * | 11/1990 | Palanisamy | .......... 428/432 |
| 6,812,821 B2 | * | 11/2004 | Fujita et al. | .......... 338/34 |
| 2001/0025484 A1 | | 10/2001 | Ueno et al. | |

FOREIGN PATENT DOCUMENTS

| JP | 05010910 A | * | 1/1983 |
|---|---|---|---|
| JP | 060194346 A | * | 10/1985 |
| JP | 2003-91840 A | * | 4/2003 |

* cited by examiner

*Primary Examiner*—Michael Cygan
(74) *Attorney, Agent, or Firm*—Sughrue Mion, PLLC

(57) ABSTRACT

A humidity-sensitive porous layer (13) of a humidity-sensitive element section (3) of a humidity sensor (1) is formed of a crystalline phase oxide grains such as $Al_2O_3$—$SnO_2$—$TiO_2$ and of a glass phase such as silicate glass covering the crystalline phase. The glass phase contains an alkali metal oxide and/or alkaline earth metal oxide such as $Li_2O$. The humidity sensitive porous layer (13) assumes a skeletal structure that is formed of crystalline phase oxide grains covered or coated with the glass phase. A heater (17) of the humidity sensor is controlled to heat the humidity-sensitive element section (3) at a temperature ranging from 500° C. to 800° C. so as to clean off the humidity-sensitive element section while an internal combustion engine is running and exhausting fouling substances. Measurement of Humidity in an exhaust gas exhausted from an exhaust gas purifying apparatus of an internal combustion engine is carried out by using the humidity sensor (1), so long as the exhaust gas temperature does not exceed 100° C. regardless of whether or not the engine is running.

28 Claims, 10 Drawing Sheets

HUMIDITY SENSOR AND METHOD OF USING THE HUMIDITY SENSOR

BACKGROUND OF THE INVENTION

1. Field of the Invention

The present invention relates to an impedance-variation-type humidity sensor for use in an exhaust gas exhausted from, for example, a smoke discharge apparatus, an exhaust duct, or an exhaust-gas purifying apparatus of an internal combustion engine, as well as to a method of using the humidity sensor in the exhaust gas.

2. Description of the Related Art

Conventionally, in order to detect humidity with high accuracy over a long period of time, the impedance-variation-type or rather resistance-variation-type humidity sensors commercially available for industrial use are periodically subjected to heat-applied cleaning so as to burn out fouling substances such as dust, deposits, carbon, coke (insufficiently fired fuel) and crystal water deposited on a humidity-sensitive element thereof.

For example, Patent Document 1 proposes a method of recovering the measuring accuracy of a humidity sensor when the measuring accuracy is lowered as a result of adhesion of tar from cigarette smoke to a humidity-sensitive element held in an ambient atmosphere. Specifically, a ceramic heater of the humidity sensor is electrically energized to heat the humidity-sensitive element to a temperature of about 500° C. for one minute or so, thereby cleaning off or burning out adhered fouling substances from the surface of the humidity-sensitive element so as to refresh the sensor element and recover the impedance of the sensor element degraded by the fouling substances formed on the surface thereof.

With regard to the resistance-variation-type humidity sensor for use in an exhaust gas atmosphere of an internal combustion engine, Patent Document 2, discloses a method of avoiding a condition under which water condensation or coking is prone to occur, by actuating a heater in accordance with an operating condition (e.g., duration of idling) of the internal combustion engine.

[Patent Document 1]

U.S. Pat. No. 4,801,211 to Yagi et al.

[Patent Document 2]

United States Patent Application Publication US 2001/0025484 A1 to Ueno et al.

3. Problems to be Solved by the Invention:

However, the inventors have found that heat-applied cleaning of the humidity sensor element under a temperature of about 500° C. as proposed in Patent Document 1 above fails to completely remove fouling substances adhered on the humidity-sensitive element of the humidity sensor when subject to an exhaust gas of an internal combustion engine, resulting in a failure to detect humidity with high accuracy and durability.

With respect to a humidity sensor applied to an internal combustion engine, the technique as described in Patent Document 2 fails to sufficiently clean the humidity sensor. This is because exhaust gas temperature is generally low at a position located under the floor of a vehicle where the humidity sensor is mounted.

However, even though the heater is energized when the engine continues to idle, the heating temperature is high enough only to evaporate condensed water adhered on the humidity sensor. In other words, the heating temperature is not sufficiently high to completely remove other fouling substances from the humidity-sensitive element, resulting in a failure to detect humidity with high accuracy over a long period of time.

SUMMARY OF THE INVENTION

It is therefore an object of the present invention to solve the above-mentioned problems of the prior art and to provide a humidity sensor capable of detecting humidity with high accuracy over a long period of time in an exhaust gas atmosphere exhausted from an internal combustion engine, as well as a method of cleaning or rather refreshing the humidity sensor held in contact with an exhaust gas exhausted from an internal combustion engine.

The above objects of the present invention have been achieved by providing:

(1) A humidity sensor (for detecting ambient humidity) comprising a humidity-sensitive element section having a humidity-sensitive element and a detection electrode formed on the humidity-sensitive element, and a heater for heating the humidity-sensitive element section. The humidity-sensitive element has a crystalline phase formed of oxide grains, and a glass phase that contains an alkali metal oxide and/or an alkaline earth metal oxide so that the heater can heat the humidity-sensitive element section at a temperature ranging from 500° C. to 1200° C. for a predetermined period of time when humidity measurement is not performed.

Preferably, the humidity-sensitive element for use in the present invention consists essentially of a crystalline phase formed of oxide grains, and a glass phase, the glass phase containing a glass component such as an alkali metal oxide and/or an alkaline earth metal oxide. Preferably, the humidity-sensitive element is configured such that the crystalline phase is covered or rather coated with the glass phase and pores are formed inside the glass phase.

Even over long-term use, the humidity-sensitive element of the present invention exhibits only a slight increase in impedance (resistance), thereby advantageously providing excellent durability. This is presumably because the humidity-sensitive element retards adhesion of fouling substances to the crystalline phase, and/or accelerates melting or rather diffusing of the fouling substances into the glass phase when the humidity sensor undergoes heat-applied cleaning. In other words, the glass phase covering the crystalline phase works as an adhesion-retarding agent and/or an absorbent of fouling substances so as to maintain a clean surface of the humidity sensitive layer and to restore impedance (resistance) of the humidity sensitive element section by applying heat to the humidity sensitive element section when the sensor has been degraded.

An alkali metal and/or an alkaline earth metal in a form of oxide is added so as to lower a softening point of the glass phase fired. Examples of suitable alkali metal oxides include $Li_2O$, $Na_2O$, $K_2O$, $Rb_2O$, and $Cs_2O$. Examples of suitable alkaline earth metal oxides include BeO, MgO, CaO, BaO, and SrO. Preferably, the alkali metal oxide and/or alkaline earth metal oxide partly forming the glass phase is in an amount of 0.5 mol % (namely 0.5% by mole) to 30 mol % of the total glass phase so that the softening temperature of the fired glass phase appears at a temperature of from 800° C. to 1200° C.

Particularly, in the present invention, the humidity-sensitive element section is heated at a temperature ranging from 500° C. to 1200° C. In other words, in the present invention, by heating the glass phase of the humidity-sensitive element section at a temperature of 500° C. or higher, adhering fouling substances or deposits, can sufficiently volatize or be cleaned off from the humidity-sensitive element section. Furthermore, so-called heat-deterioration of the humidity-sensitive element section can be prevented; specifically, heat-induced ceramic grain growth can be suppressed, loss of electrode material (e.g., platinum) can be prevented, and excessive increase in impedance (resistance) of the humidity sensor can be prevented. For reliably enhancing these effects, a heating temperature range of 650° C. to 800° C. for restoring the impedance of the humidity sensitive element section is most preferable. Notably, the temperature at which the humidity measurement is conducted by this humidity sensor is restricted to a temperature range such that the impedance of the humidity sensitive element does not become excessively high. For this reason, the temperature at which the humidity measurement is conducted generally cannot exceed 100° C. In other words, only when the exhaust gas temperature is below 100° C. (which low temperature occurs during a short period of time just after the engine starts rotating), is the humidity sensor according to the invention used to analyze a state of an internal combustion engine including an exhaust gas purification apparatus thereof based on the humidity of a low temperature exhaust gas. Since the humidity measurement is not conducted when the engine is exhausting at a high gas temperature exceeding 100° C., according to the invention, the humidity sensor in contact with the high temperature exhaust gas containing fouling substances may be operated to exercise its self-cleaning capability while the engine is running and exhausting fouling substances. This cleaning capability is assisted by a heater or heating means for heating the humidity sensitive element section at a temperature of 500–800° C., according to an aspect of the invention, so that the fouling substances burn out and do not adhere to the surface of the humidity sensitive element section of the sensor. This is done at a time during which the humidity measurement can not be conducted, namely, while driving the engine and exhausting a high temperature gas exceeding 100° C. Just after the engine is stopped and when no further new fouling substances are exhausted therefrom, the heater may optionally heat the humidity sensitive element section to a temperature of from higher than 800° C. to 1200° C. for a short period of time so that complete cleaning or rather further refreshing of the surface of humidity sensitive porous layer is attained and assured for the next humidity measurement (when the engine restarts, exhausting a low temperature gas again).

Impedance of the humidity-sensitive element is detected by applying AC voltage across electrodes of the humidity-sensitive element section, and a resistance of the humidity-sensitive element is detected by applying DC voltage across the electrodes of the humidity-sensitive element section. Humidity sensors according to the invention measure humidity (relative humidity and/or absolute humidity) based on variation in impedance (and/or resistance) of the humidity-sensitive element section. Notably, impedance and resistance differ merely in that the applied voltage is AC voltage or DC voltage. The below description representatively uses the term "impedance" to encompass both impedance and resistance.

Material whose impedance varies with moisture or rather humidity (e.g., as humidity increases, impedance decreases) is used to form the crystalline phase formed of oxide grains. Examples of such material include oxide ceramic materials such as $Al_2O_3$, $TiO_2$ and $SnO_2$, and preferable examples of the crystalline phase include grains of $Al_2O_3$, $Al_2O_3$—$TiO_2$ and $Al_2O_3$—$TiO_2$—$SnO_2$.

The predetermined period of time may be determined as appropriate in accordance with the condition of adhesion of fouling substances or deposits and the degree of removal of adhering fouling substances.

Preferably, in order to prevent adhesion of fouling substances to the humidity-sensitive element, a porous protection layer is formed on the surface of the humidity-sensitive element.

(2) In a preferred embodiment the present invention provides a humidity sensor according to (1) above, wherein the humidity-sensitive element is a porous element comprising the crystalline phase and the glass phase; the crystalline phase forms a skeletal structure of the porous element; and a surface of the skeletal structure is covered or coated with the glass phase.

In this embodiment, the humidity-sensitive element is porous; the crystalline phase formed of an oxide or oxides (e.g., a crystalline phase formed of an oxide grain, or a crystalline phase formed of mutually bonded oxide grains) forms a skeletal structure; and the surface of the skeletal structure is coated with the glass phase that contains a glass component including an alkali metal oxide or an alkaline earth metal oxide in addition to silicate glass, phosphate glass and/or borate glass.

Thus, even over long-term use, the humidity-sensitive element exhibits only a slight increase in impedance, thereby providing excellent durability.

(3) In yet another embodiment, the present invention provides a humidity sensor according to (1) or (2) above, wherein the detection electrode is a platinum electrode that contains more than 80% by weight of platinum and the rest of oxide (e.g. $ZrO_2$ and/or $Al_2O_3$). In the present embodiment, the detection electrode is formed predominantly of platinum. Platinum exhibits excellent durability when used in an atmosphere of an exhaust gas component exhausted from, for example, an internal combustion engine of an automobile, or in a high-temperature atmosphere.

The detection electrode can assume the form of, for example, at least a pair of electrodes provided on the surface of the humidity-sensitive element.

(4) In yet another preferred embodiment, the present invention provides a humidity sensor according to any one of (1) to (3) above, wherein the glass component of the glass phase includes at least one of silicate glass, phosphate glass and borate glass, in addition to the alkali metal oxide and/or the alkaline earth metal oxide.

(5) In yet another preferred embodiment, the present invention provides a humidity sensor according to any one of (1) to (4), wherein the glass phase has a softening point of 800° C. to 1,200° C.

A softening point of the glass phase of 800° C. or higher lowers the possibility that the glass phase might melt when cleaning is performed upon application of heat from the heater. A melting point of the glass phase of 1,200° C. in production of the humidity-sensitive element through firing allows a sufficient softening of the glass phase, so that the skeletal structure (i.e., the crystalline phase coated with the glass phase) can be reliably maintained.

Notably, in the case that the heating temperature of the heater is set to 800° C., a glass phase having a softening point of more than 800° C. is necessarily employed.

(6) In yet another preferred embodiment, the present invention provides a humidity sensor according to any one of (1) to (5) above, wherein an amount of 10 mol % to 56 mol % of the glass phase is contained in the humidity-sensitive porous layer.

In the present embodiment, because the glass-phase content is 10 mol % or more, the humidity sensor is hardly susceptible to fouling substance or deposits, so that variation in impedance of the humidity sensor is small, thereby providing high durability. Since the glass-phase content is 56 mol % or less, the initial impedance of the humidity sensor can be suppressed to a low level, thereby facilitating circuit design. For enhancing these effects, a more preferred glass-phase content is 12.5 mol % to 50 mol % in the humidity sensitive porous layer, and the rest is the crystalline phase content.

(7) In yet another preferred embodiment, the present invention provides a humidity sensor according to any one of (1) to (6) above, wherein the humidity sensor is used to make measurements in exhaust gas of an internal combustion engine.

A humidity sensor subjected to automotive exhaust gas is exposed to a very severe atmosphere that contains, in large amounts, various gas components; deposit components such as Ca, P and Mo derived from engine oil; gasoline components; carbon; water; and other components. However, each of the above described embodiments of the invention enables humidity measurement with high accuracy over a long period of time.

The humidity sensor of the present invention can be used not only to detect humidity in exhaust gas but also in an atmosphere of a smoke-extraction apparatus or an exhaust duct. Also, the humidity sensor can be used to detect humidity in, for example, an atmosphere of low oxygen concentration or an atmosphere that contains a reducing gas.

(8) In yet another preferred embodiment, the present invention provides a humidity sensor according to (7) above, wherein the humidity sensor is used to detect, from temperature variation of exhaust gas, a condition of an exhaust-gas-purifying apparatus (e.g., adsorptive material capable of adsorbing hydrocarbon and water, exhaust-gas purification material such as a three-way catalytic converter, or HC trap material employing a zeolite that absorbs or rather adsorbs moisture) used in the internal combustion engine.

(9) In yet another preferred embodiment, the present invention provides a humidity sensor according to any one of (1) to (8) above, wherein, during a time when the humidity measurement is not performed, the humidity-sensitive element section is heated at all times.

By heating the humidity-sensitive element section at all times as described above, fouling substances can be sufficiently removed.

(10) In yet another preferred embodiment, the present invention provides a humidity sensor according to (7) or (8) above, wherein, after the internal combustion engine is stopped, the humidity-sensitive element section is heated for a predetermined short period of time.

The effect of heating the humidity-sensitive element section by the heater is obtained even when heating is performed while the internal combustion engine is in operation, and is stopped as soon as the internal combustion engine is stopped. However, the effect of heating is enhanced when performed for a predetermined period of time after the internal combustion engine is stopped. This is because, immediately after the internal combustion engine is stopped, dust, depositing substances, carbon, splashing water, and the like are present in an atmosphere in the vicinity of the humidity sensor. Therefore, according to the present embodiment, after the internal combustion engine is stopped, the humidity-sensitive element section is heated for a predetermined period of time (e.g., several seconds to several minutes).

In this case, the heater may be energized for several seconds to about 10 minutes, whereby the effect of heating is sufficiently obtained. Energization of the heater may be continued even after the internal combustion engine is stopped, or may be suspended for a predetermined period of time (e.g., until a water temperature sensor for detecting the temperature of cooling water for the internal combustion engine indicates a temperature of 50° C. or lower) after the internal combustion engine is stopped, and then resumed.

(11) In yet another preferred embodiment, the present invention provides a humidity sensor according to (10) above, wherein, after the internal combustion engine is stopped, the humidity-sensitive element section is heated at a temperature ranging from 500° C. to 1,200° C. for refreshing. Heating at a temperature within the above range can remove fouling substances almost completely.

When the heating (e.g., heating after the internal combustion engine is stopped) is to be performed, heating temperature and/or duration may be set in accordance with a value indicative of the condition of the humidity sensor.

When fouling substances adhere to the humidity sensor in large amounts, an increase in the heating temperature or like adjustment is required. Thus, the degree of fouling of the humidity sensor is detected; e.g., a value (a measured value) corresponding to the degree of fouling of the humidity sensor, such as impedance of the humidity sensor, is detected. On the basis of the detected value, heating temperature and duration (i.e., the condition of energization of the heater) are adjusted. In this manner, fouling substances can be sufficiently removed at all times, irrespective of the condition of fouling of the humidity sensor.

(12) In yet another preferred embodiment, the present invention provides a humidity sensor according to any one of (1) to (11) above, wherein a resistor-type temperature sensor is used as a temperature detection means for detecting a temperature of the humidity-sensitive element section; and the heater is controlled such that the temperature detection means assumes a predetermined resistance.

In order to energize the heater for heating the humidity-sensitive element section, a predetermined constant voltage, for example, can be applied to the heater. In this case, the humidity-sensitive element section may fail to assume an expected appropriate temperature, depending on the temperature of exhaust gas or the like.

In the case where heater control is performed while the applied voltage to the heater is kept constant, the temperature of the humidity-sensitive element section may vary depending on the operating condition of the internal combustion engine. When the temperature becomes excessively low (while falling outside the aforementioned preferred temperature range), the function of preventing adhesion of fouling substances is impaired. Conversely, when the temperature becomes excessively high, a humidity-sensitive material and an electrode material become highly likely to disadvantageously exhibit grain growth, segregation, degradation, or the like.

In order to cope with the above problem, the present invention utilizes a property of the heater or the resistor-type temperature sensor wherein resistance varies with temperature. Specifically, the heater is subjected to feedback control in accordance with the resistance of the temperature detection means, e.g., such that the resistance becomes constant.

For example, when the resistance of the temperature detection means becomes large, this indicates that the temperature of the humidity-sensitive element section is high; thus, heating by the heater is suppressed. Conversely, when the resistance of the temperature detection means becomes small, this indicates that the temperature of the humidity-sensitive element section is low; thus, heating by the heater is accelerated. In this manner, the humidity-sensitive element section can be heated at an appropriate temperature at all times.

Preferably, an operating condition of the internal combustion engine including an exhaust gas purifying apparatus incorporating a catalyst therein is detected, and the heater is controlled in accordance with the detected operating condition.

Since the temperature of exhaust gas varies depending on an operating condition of the internal combustion engine, the temperature of the humidity-sensitive element section also varies depending on an operating condition of the internal combustion engine. Thus, the duration of voltage application to the heater and applied voltage, for example, are adjusted in accordance with an operating condition, such as intake pressure (negative pressure), vehicle speed, or engine speed. In this manner, the humidity-sensitive element section can be heated at a temperature falling within an appropriate temperature range.

(13) In a second aspect, the present invention provides a method for measuring humidity using a humidity sensor comprising a humidity-sensitive element section having a humidity-sensitive element and a detection electrode, and a heater for heating the humidity-sensitive element section, wherein the humidity-sensitive element comprises a crystalline phase formed of an oxide, and a glass phase that contains, a glass component including an alkali metal oxide and/or an alkaline earth metal oxide; during a time when humidity measurement is not performed, the heater heats the humidity-sensitive element section at a temperature ranging from 500° C. to 800° C. and/or higher than 800° C. to 1200° C. for a predetermined period of time, and humidity measurement is carried out when a temperature of a gas such as an exhaust gas contacting the humidity-sensitive element is not higher than 100° C.

An important feature of the method for measuring humidity of an exhaust gas exhausted from an internal combustion engine, using a humidity sensor of the present invention is that when the engine is operating and exhausting a high temperature exhaust gas, humidity measurement is not carried out. At this time the heater is heating the humidity sensitive porous layer of the sensor to a temperature of 500° C. to 800° C. so as to prevent degradation of the humidity sensitive porous layer, and the humidity measurement is carried out only when the temperature of the gas is not higher than 100° C. Although the heater may heat the humidity sensitive porous layer intermittently or continuously (preferable) so long as the engine is running, the humidity measurement is carried out so long as the exhaust gas temperature does not exceed 100° C. regardless of whether or not the engine is running.

Figure 1:
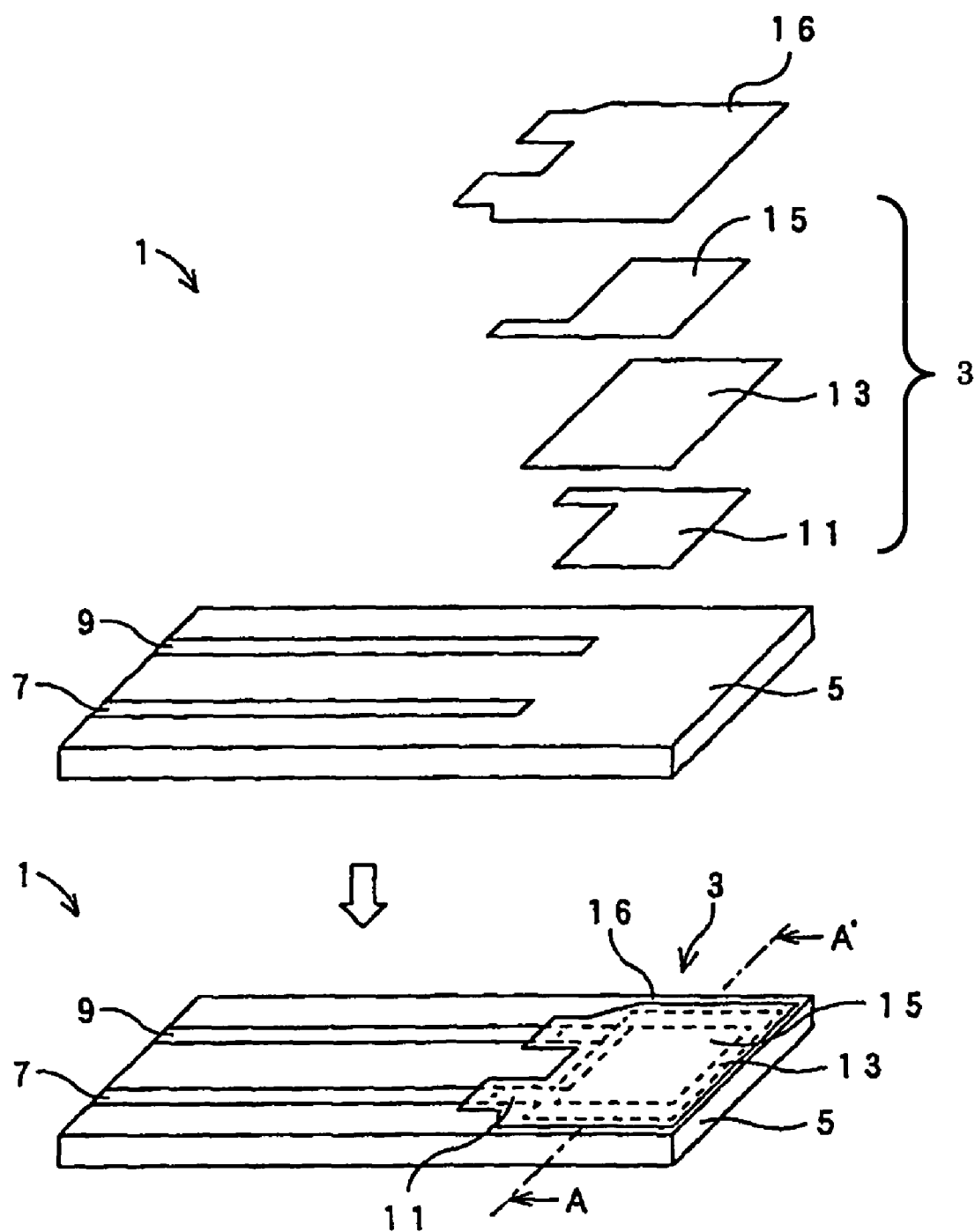
FIG. 1 is an explanatory view showing a humidity-sensitive element section of a humidity sensor of an embodiment of the present invention in an assembled condition and in an exploded condition.

Reference Numerals are used to identify various elements of the drawings as defined below:

1 . . . humidity sensor
3 . . . humidity-sensitive element section
5 . . . insulating substrate
7, 9 . . . lead portion 11 . . . lower electrode
13 . . . humidity-sensitive porous layer
15 . . . upper electrode
16 . . . protection layer
17 . . . heater
19 . . . temperature-measuring resistor (temperature sensor)

DESCRIPTION OF THE PREFERRED EMBODIMENTS

The present invention will next be described in greater detail by reference to the drawings and the following embodiment. However, the present invention should not be construed as being limited thereto.

Figure 2:
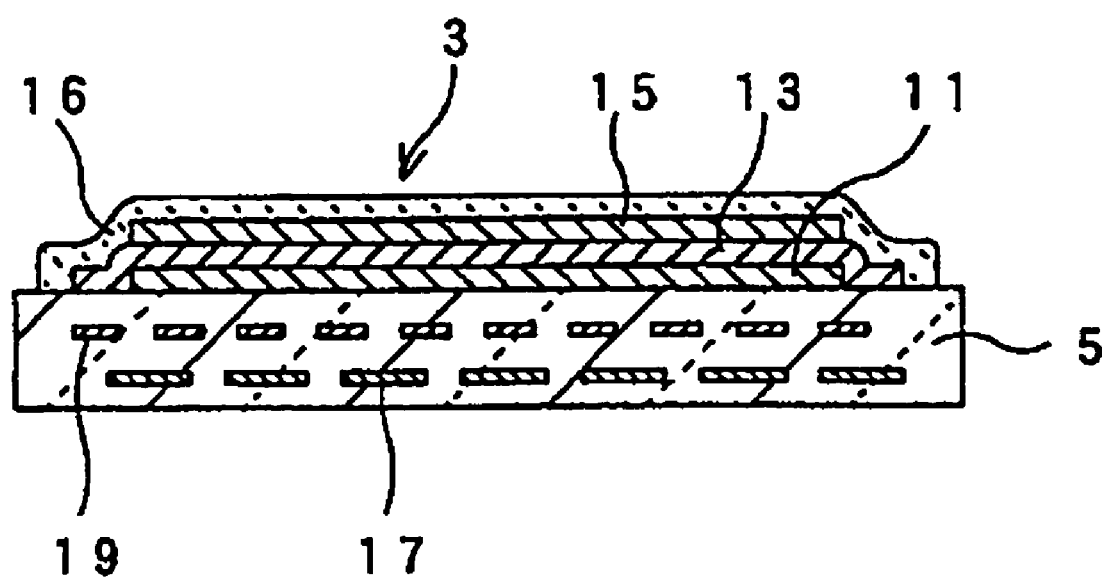
FIG. 2 is a sectional view of the humidity-sensitive element section taken along line A–A' of FIG. 1.

Embodiment 1:

a) First, the configuration of a humidity sensor of the present embodiment will be described. FIG. 1 is a perspective view showing the humidity sensor in an assembled condition and in an exploded condition. FIG. 2 is a sectional view taken along line A–A' of FIG. 1.

As shown in FIG. 1, the humidity sensor 1 is an impedance-variation-type humidity sensor; and a humidity-sensitive element section 3, which is an essential portion of the humidity sensor 1, is configured such that component elements are laminated on an insulating substrate 5 made of alumina, as described below.

A pair of lead portions 7 and 9 is disposed on the insulating substrate 5; a lower electrode 11 is disposed in contact with the lead portion 9; a humidity-sensitive porous layer (or rather moisture-sensitive layer) 13 formed of a humidity-sensitive material is disposed on the lower electrode 11; an upper electrode 15 is disposed on the humidity-sensitive layer 13, in contact with the lead portion 7; and a protection layer 16 is disposed on the upper electrode 15 in such a manner as to cover all of the lower electrode 11, the humidity-sensitive layer 13, and the upper electrode 15.

As shown in FIG. 2, a heater 17 for heating the humidity-sensitive element section 3, and a temperature sensor 19, which is a temperature-measuring resistor, are disposed within the insulating substrate 5. The heater 17 is formed predominantly of platinum, and the temperature sensor 19 is also formed predominantly of platinum.

The lower electrode 11 and the upper electrode 15 are layers each having a thickness of about 15 μm and are formed by means of thick-film printing. The lower and upper electrodes 11 and 15 are porous detection electrodes that are formed predominantly of platinum.

The humidity-sensitive layer 13 is a porous layer having a thickness of about 0.03 mm and is formed by means of thick-film printing. The humidity-sensitive layer 13 is formed predominantly of $Al_2O_3$—$SnO_2$—$TiO_2$, which is a humidity-sensitive material. The impedance of the humidity-sensitive material varies with humidity of an ambient atmosphere (specifically, as the humidity increases, the impedance is lowered).

Figure 3:
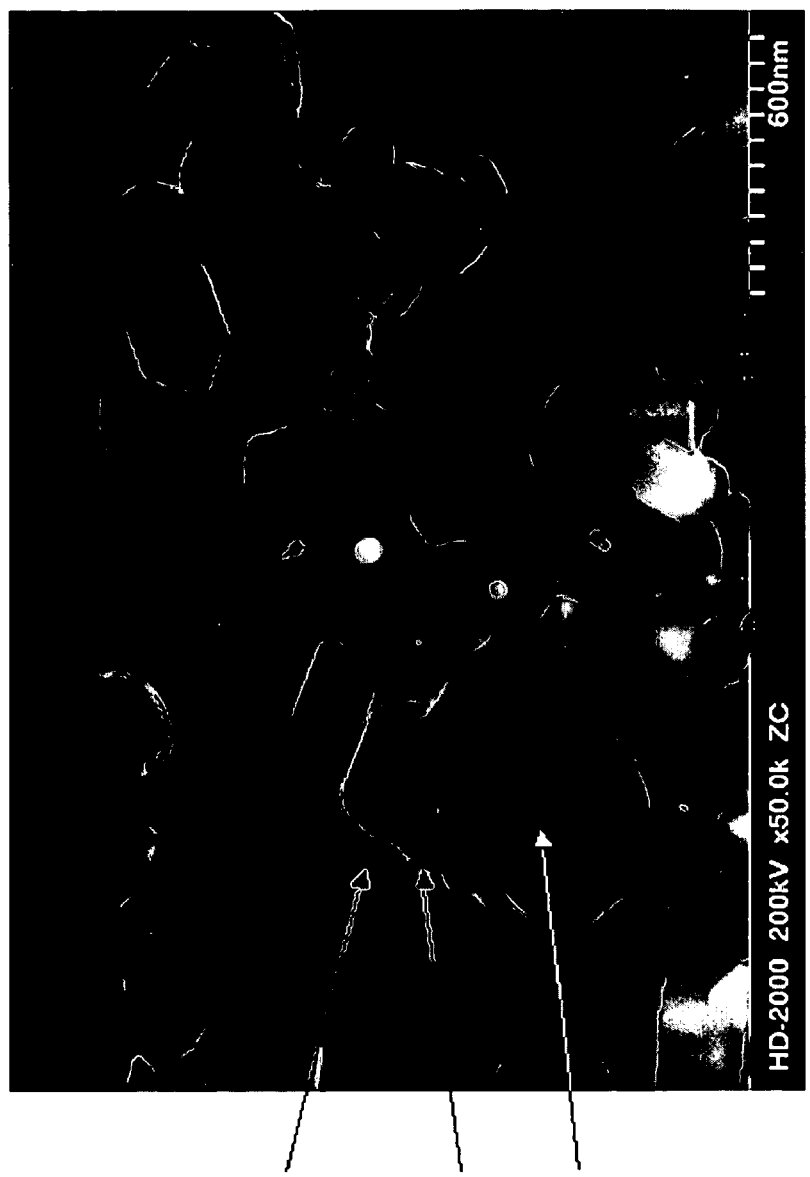
FIG. 3 is a photograph showing a view observed, through TEM (Transmission Electron Microscopy), of the humidity-sensitive porous layer of Experiment Example 2.
Figure 4:
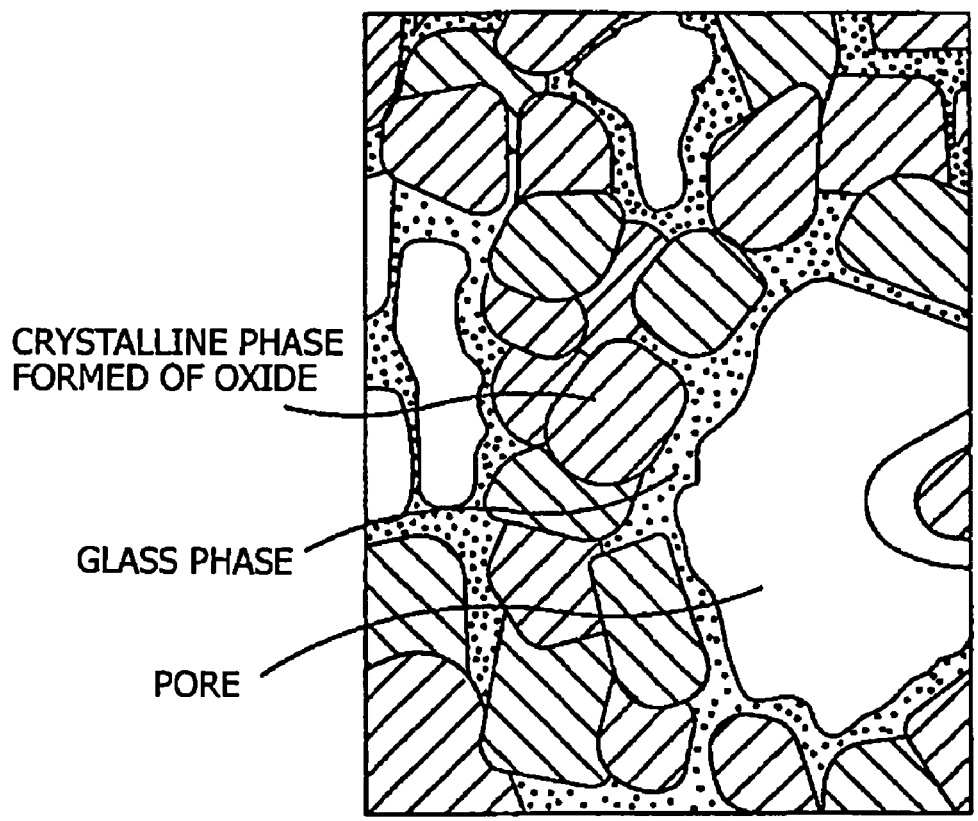
FIG. 4 is a schematic diagram showing a portion of the photograph of FIG. 3.

Specifically, as shown in a transmission electron micrograph (TEM photograph) of FIG. 3 and in FIG. 4, which is a schematic diagram of the micrograph, the humidity-sensitive layer 13 is composed of crystalline oxide grains of $Al_2O_3$—$SnO_2$—$TiO_2$ having an average grain size ranging from 100 nm to 500 nm, a glass phase that contains an oxide of an alkali metal such as Li (or an oxide of an alkaline earth metal), and a number of pores. A softening point (or rather softening temperature) of the glass phase ranges from 800° C. to 1,200° C.

In other words, the humidity-sensitive layer 13 is advantageously composed of a porous skeletal structure, which is formed of a crystalline phase formed of a number of crystalline oxide grains, and a glass phase that covers the surface of the crystalline oxide grains and forms pores in the glass phase. In this manner, the humidity-sensitive layer 13 assumes a porous complex structure.

The protection layer 16 is a porous protection film having a thickness of about 30 μm that is formed predominantly of $MgAl_2O_4$ by means of thick-film printing. The protection layer 16 is advantageously adapted to prevent intrusion of dust or the like to the lower electrode 11, to the humidity-sensitive layer 13, and to the upper electrode 15.

b) Next, a method of producing the humidity sensor 1 will be described.

(1) Method of producing a mixed powder as material for the humidity-sensitive layer 13

First, butoxy Al, butoxy Ti, and butoxy Sn, of 99.0 wt. % or higher purity are measured out at predetermined proportions (e.g., at a 6:2:2 weight ratio). These substances are dissolved in butanol. The resultant solution is heated to a temperature of 120° C. or higher.

Next, pure water is gradually added to the solution while the solution is stirred. Subsequently, the solution is further stirred, allowing reaction for about one hour. That is, the aforementioned alkoxides are hydrolyzed.

Subsequently, the resultant precipitate is collected, dried, and then calcined. Thus, a crystalline powder of $Al_2O_3$—$SnO_2$—$TiO_2$ is thus obtained.

Next, this crystalline powder is immersed in a predetermined amount in butanol (so as to form crystalline phase grains in the humidity-sensitive layer 13), and a butoxy Al, a butoxy Si, and $LiOC_2H_5$ are added therein in a predetermined amount (so as to form a glass phase in the humidity-sensitive layer 13). The resultant solution is hydrolyzed in a similar manner as described in the case of forming the powder of $Al_2O_3$—$SnO_2$—$TiO_2$. The resultant precipitate is collected, dried, and calcined. A mixed powder is thus obtained that serves as a humidity-sensitive material for the next step.

(2) Method of producing the humidity-sensor 1

First, the lower electrode 11 is formed on an insulating substrate 5 that is formed of $Al_2O_3$. Specifically, a pattern of the lower electrode 11 is printed on the insulating substrate 5 using a Pt-based paste, followed by drying at 120° C. for 15 minutes and then firing at 1,200° C. for 10 minutes.

Next, the humidity-sensitive layer 13 is formed on a lower electrode 11. Specifically, a pattern of the humidity-sensitive layer 13 is printed on the lower electrode 11 using a paste of the aforementioned mixed powder, followed by drying at 60° C. for 1 hour and then firing at 1,200° C. for 2 hours.

Next, the upper electrode 15 is formed on the humidity-sensitive layer 13. Specifically, a pattern of the upper electrode 15 is printed on the humidity-sensitive layer 13 using a Pt-based paste, followed by drying at 120° C. for 15 minutes and then firing at 1,200° C. for 10 minutes.

Next, the protection layer 16 is formed on the upper electrode 15. Specifically, a pattern of the protection layer 16 is printed on the upper electrode 15 using a paste of spinel ($MgAl_2O_4$) powder, followed by drying at 60° C. for 1 hour and then firing at 1,200° C. for 2 hours.

Thus, the humidity sensor 1 is completed in the form of a fired or rather sintered body.

c) Next, a control unit for controlling the above-described humidity sensor 1 will be described.

Figure 5:
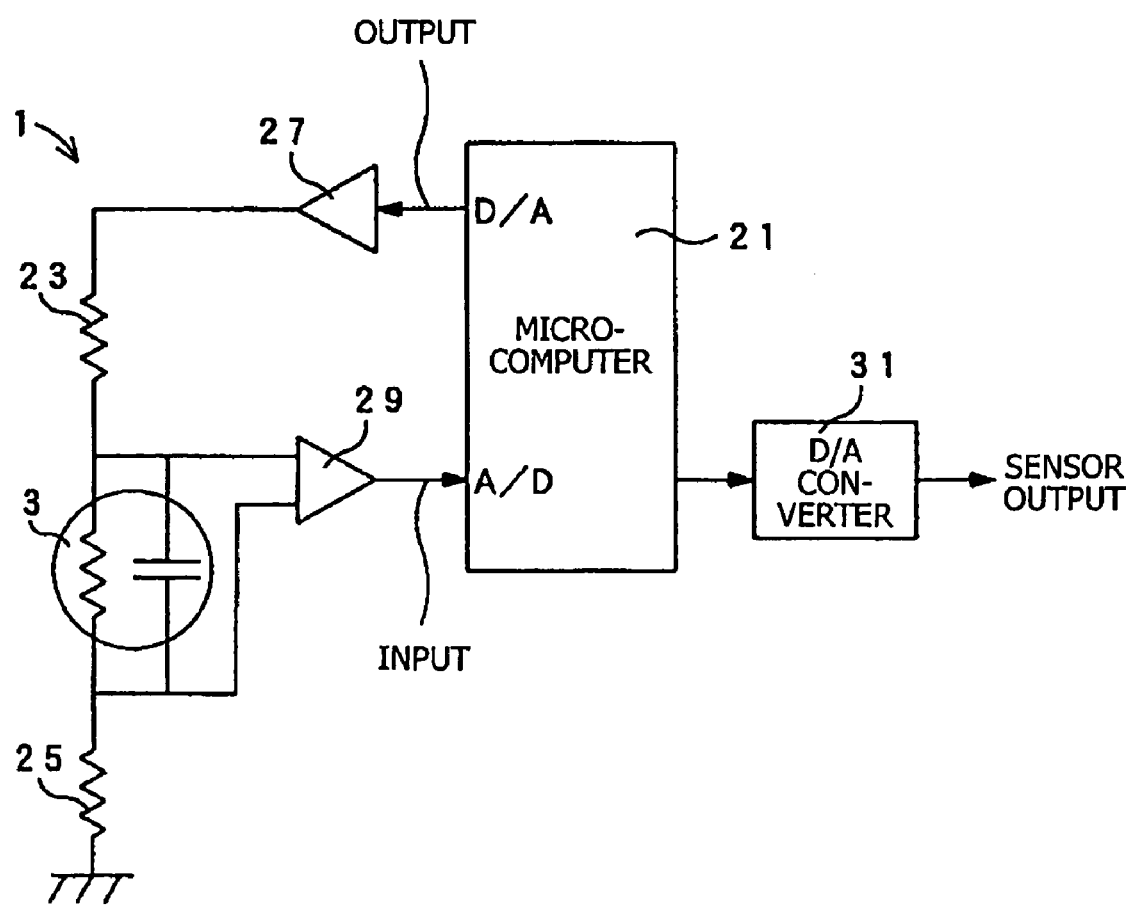
FIG. 5 is an explanatory diagram showing a circuit configuration for measuring humidity.

As shown in a circuit configuration of FIG. 5 for measuring humidity, the humidity-sensitive element section 3 of the humidity sensor 1 is connected to a microcomputer 21 which receives an output of the humidity-sensitive element section 3. The output corresponds to impedance of the humidity-sensitive element section 3, and is set such that the sensor output increases with increasing impedance.

Specifically, a first comparative resistor 23, the humidity-sensitive element section 3 (of the humidity sensor 1), and a second comparative resistor 25 are connected in series. An AC voltage; for example, $V_{p-p}$=2 V, frequency 100 Hz, is applied to the first comparative resistor 23, the humidity-sensitive element section 3, and the second comparative resistor 25 via a buffer 27 from a D/A section (digital-to-analog conversion section) of the microcomputer 21. An AC voltage (AC voltage fraction) obtained between opposite ends of the humidity-sensitive element section 3 is input to an A/D section (analog-to-digital conversion section) of the microcomputer 21 via an operational amplifier 29. Furthermore, the microcomputer 21 outputs a sensor output via a D/A converter 31.

Figure 6:
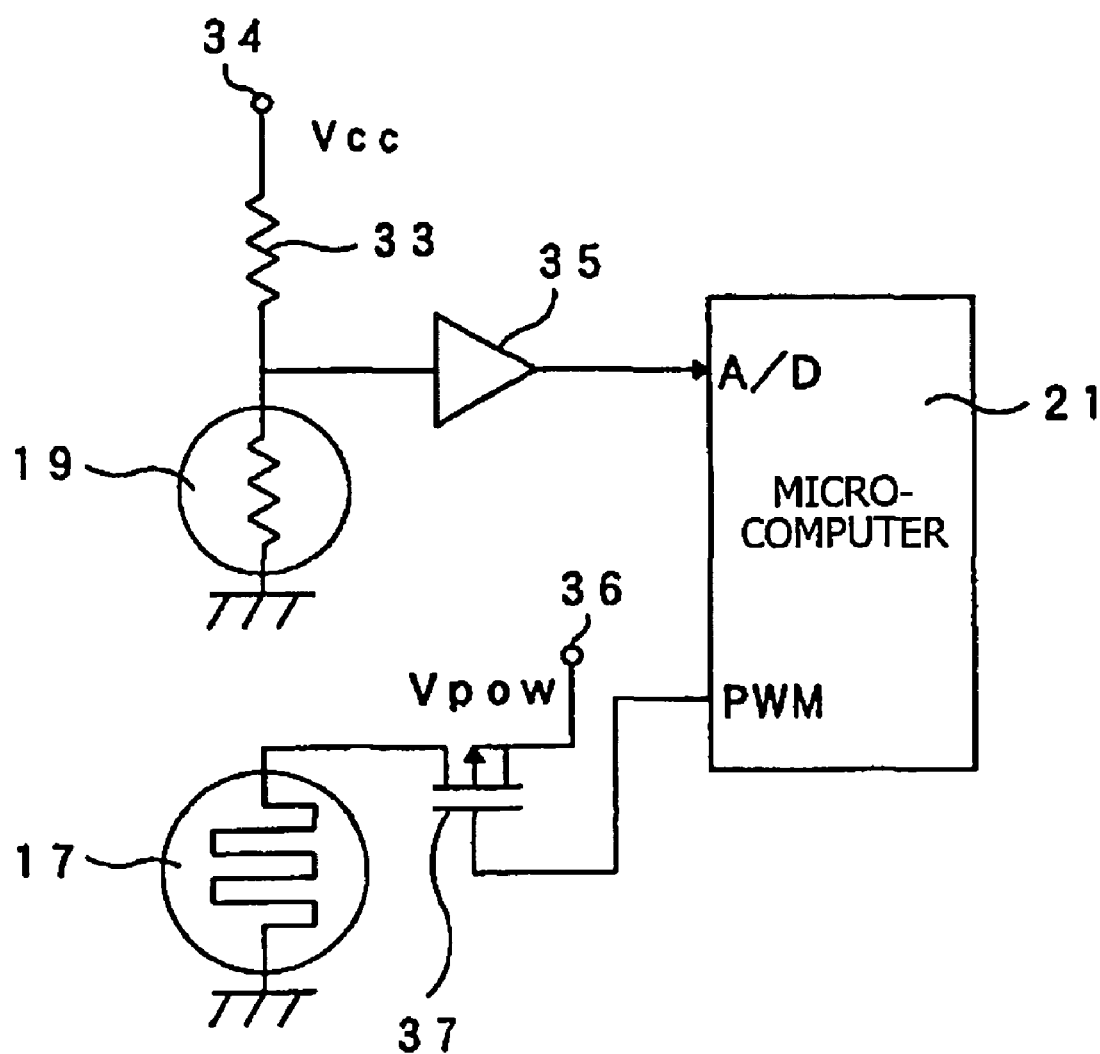
FIG. 6 is an explanatory diagram showing a circuit configuration for controlling a heater.

As shown in the circuit configuration of FIG. 6 for controlling the heater 17, the temperature sensor 19 and a comparative resistor 33 are connected in series; and a reference voltage is applied to the temperature sensor 19 and the comparative resistance 33 from a power supply 34. Voltage (potential difference) of the temperature sensor 19 is input to an A/D section (analog-to-digital conversion section) of the microcomputer 21 via an operational amplifier 35.

The heater 17 is connected to the microcomputer 21 via a switch element 37, and a constant voltage 36 ($V_{pow}$) is applied to the heater 17 in accordance with a signal issued from a signal output section (PWM) of the microcomputer 21. For example, the heater 17 can be turned on/off in cycles of 32 ms with a duty ratio of 90% or less. Thus, the resistance of the temperature sensor 19 (therefore, ambient temperature) can be measured for the duration of the heater 17 being off.

Notably, for convenience of description, the microcomputer 21 appears in both of FIGS. 5 and 6. Usually, the same microcomputer 21 is used for both measuring temperature and control of the heater 17. Also, two different microcomputers 21 may be used.

In the present embodiment, the above-mentioned control unit for the humidity sensor 1 is operated such that, during a time when humidity measurement is not performed (when the internal combustion engine is running and exhausting a high temperature gas having a temperature exceeding 100° C.), the heater 17 is energized so as to heat the humidity-sensitive element section 3 at a temperature ranging from 500° C. to 800° C. Notably, after the engine is stopped, the heater 17 can heat the humidity-sensitive element beyond the temperature of 800° C. up to 1200° C. for further complete cleaning or refreshing.

Specifically, the above-described circuit configuration for controlling the heater 17 is designed to adjust voltage to be applied to the heater 17, such that the resistance of the temperature sensor 19, which is a temperature-sensing resistance element, coincides with the resistance of the heater 17 as measured when the heater 17 assumes a predetermined control temperature.

Thus, the temperature of the humidity sensor 1 (particularly, the temperature of the humidity-sensitive element section 3) can be held within an appropriate range as suggested above, so that adhering fouling substances or deposits, do not adhere to or can be sufficiently removed from the humidity-sensitive element section 3.

EXPERIMENT EXAMPLE 1

Next, experiments will be described that were conducted in order to confirm the effect of the present embodiment.

Experiment Example 1 confirms the significance of the amount of glass and the effect of heating by the heater.

Specifically, a plurality of humidity sensors (which differed in crystalline-phase component of the humidity-sensitive element) were prepared, having a structure similar to that of the above embodiment within the scope of the present invention. The thus-produced humidity sensors, which served as Examples of the invention, were tested for their humidity sensing characteristics in accordance with the procedure described below in (1) to (3) below.

(1) Heat-applied cleaning (heating at 750° C. for 2 minutes) in preparation for measurement was performed. Subsequently, the impedance across each of the humidity sensors was measured between opposite electrodes by use of the shunt-type evaluation method specified in JIS Z 8806 (1981), incorporated herein by reference, thereby obtaining initial humidity sensing characteristics of the humidity sensors.

Figure 7:
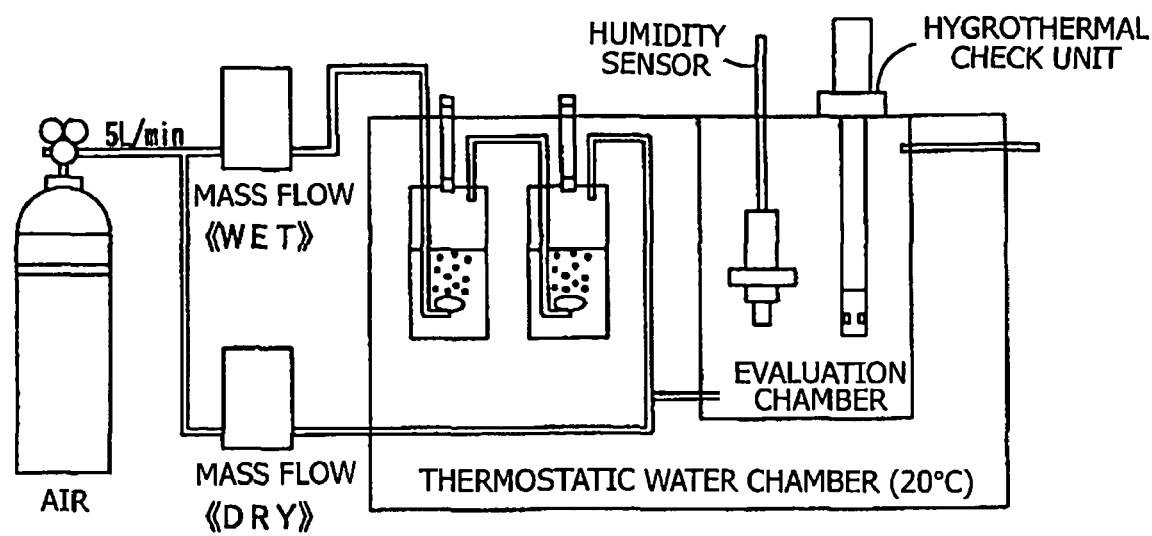
FIG. 7 is an explanatory diagram showing an experimental apparatus used in a shunt-type evaluation method.

The shunt-type evaluation method is schematically shown in FIG. 7. Air, which served as an evaluation gas, was supplied at 5 L/min; the addition amount of water was adjusted; measurement humidity was set to 20 RH %; and measurement temperature was set to 20° C. Then, the impedance of the humidity sensors was measured.

(2) Next, the humidity sensors were attached within an exhaust pipe of an automobile vehicle so as to contact the exhaust gas. The automobile vehicle was put through a driving test (the automobile on a chassis dynamometer was driven in accordance with about a 300 km driving pattern representative of driving through an urban area and on an expressway).

The humidity sensors that had undergone the above driving test were subjected to heat-applied cleaning (heating at 750° C. for 2 minutes) in preparation for measurement. Subsequently, by use of the shunt-type evaluation method as used above in (1), the humidity sensors were measured for humidity sensing characteristics, whereby humidity sensing characteristics of the humidity sensors after the durability test were obtained.

(3) On the basis of impedance (A) of each of the humidity sensors as measured in the initial state (before the durability test) and impedance (B) of each of the humidity sensors as measured after the durability test, the rate of change or rather variation of impedance (B/A) was calculated. The rate of change of impedance is shown below in Table 1.

Meanwhile, humidity sensors outside the scope of the present invention and serving as Comparative Examples were prepared, having a structure similar to that of Embodiment 1 except not containing a glass component. In accordance with the measuring procedure described above in (1) to (3), the humidity sensors of the Comparative Examples were measured for humidity sensing characteristics at an initial state and after the driving test (after the durability test). The results of measurement are also shown below in Table 1.

In Experiment Example 1, temperature control was performed on the heater during the driving test, whereby heat-applied cleaning was carried out at a cleaning temperature of 750° C.

TABLE 1

| Sample No. | | Crystalline Phase ($Al_2O_3$—$TiO_2$—$SnO_2$) [mol %] | Glass Phase [mol %] | Rate of Change of Impedance |
|---|---|---|---|---|
| 1 | Comparative Example 1 | 100 | 0 | 5.53 times |
| 2 | Example 1 | 80 | 20 | 1.03 times |
| | | Crystalline Phase ($Al_2O_3$—$TiO_2$) [mol %] | | |
| 3 | Comparative Example 2 | 100 | 0 | 84.3 times |
| 4 | Example 2 | 80 | 20 | 1.40 times |
| | | Crystalline Phase ($Al_2O_3$) [mol %] | | |
| 5 | Comparative Example 3 | 100 | 0 | 10.7 times |
| 6 | Example 3 | 80 | 20 | 1.12 times |

The glass phase contained in the humidity porous layers of Examples 1–3 in Table 1 constituted about 20 mol % of the humidity sensitive porous layer: approximately, 14 mol % of $SiO_2$, 2 mol % of $Li_2O$ and 4 mol % of $Al_2O_3$ as determined by use of Inductively Coupled Plasma Emission Spectrometry for analyzing elements and amounts thereof.

As is apparent from Table 1, in the case of the humidity sensors of the Comparative Examples (Sample Nos. 1, 3 and 5 whose humidity-sensitive layers did not contain a glass phase), impedance as measured after the driving test undesirably exhibited a large increase as compared to that measured before the test.

In contrast, in the case of the humidity sensors of the Examples of the invention (Sample Nos. 2, 4 and 6 whose humidity-sensitive porous layers had the glass phase), even after a 300 km run of the vehicle engine, only a slight increase in impedance was measured.

The above test results confirm that the presence of the glass phase contributes greatly to suppression of variation in impedance of a humidity sensor subjected to an environment of an automotive exhaust gas.

EXPERIMENT EXAMPLE 2

Next, Experiment Example 2 will be described.

Experiment Example 2 confirms the effect of the glass content.

Specifically, as shown below in Table 2, humidity sensors having the same crystalline-phase composition and different glass-phase contents as described in the Embodiment 1 were prepared. In a manner similar to that of Experiment Example 1, the thus-prepared humidity sensors were measured for initial humidity sensing characteristics (impedance) by use of the shunt-type evaluation method specified in JIS Z 8806 (1981).

The humidity sensors were exposed for 30 hours to exhaust gas that was generated from fuel to which a predetermined phosphorus species was added in a predetermined amount. Subsequently, in a manner similar to that of Experiment Example 1, the humidity sensors were measured for humidity sensing characteristics (impedance) using the shunt-type evaluation method specified in JIS Z 8806 (1981), whereby humidity sensing characteristics (impedance) after the durability test were obtained. Notably, humidity including relative humidity (RH) is computed as a function of the impedance measured across the electrodes formed on the humidity sensitive porous layer, which impedance varies with humidity of the gas. The impedance variation caused by factors other than the humidity, therefore, is related to accuracy of the humidity measurement. On the basis of the above-measured values of impedance, the rate of change of impedance was obtained for evaluation. The results of the calculation are shown below in Table 2.

TABLE 2

| Sample No. | | Crystalline Phase $(Al_2O_3—TiO_2—SnO_2)$ [mol %] | Glass Phase [mol %] | Rate of Change of Impedance |
|---|---|---|---|---|
| 7 | Comparative Example 1 | 100 | 0 | 822 times |
| 8 | Example 4 | 97.6 | 2.4 | 69.4 times |
| 9 | Example 5 | 93.5 | 6.5 | 15.5 times |
| 10 | Example 6 | 88.9 | 11.1 | 8.27 times |
| 11 | Example 7 | 80 | 20 | 7.22 times |
| 12 | Example 8 | 66.7 | 33.3 | 1.76 times |
| 13 | Example 9 | 44.4 | 55.6 | 2.71 times |
| 14 | Example 10 | 40 | 60 | 4.85 times |

Comparative Example 1 in Tables 1 and 2 are the same.

As is apparent from Table 2, among Examples 4 to 10, Example 6 to 9, whose glass-phase content was 11.1 mol % to 55.6 mol %, exhibited an acceptable rate of change of impedance and accordingly high durability since the respective rates of impedance change are less than 10 times that of the original impedances.

For reference, the glass phase content in Example 4 consisted of 0.2 mol % of $Li_2O$, 1.7 mol % of $SiO_2$ and the rest $Al_2O_3$ and the crystalline phase content in Example 4 consisted of 71.5 mol % of $Al_2O_3$, 5.2 mol % of $SnO_2$ and 20.8 mol % of $TiO_2$, as determined by use of Inductively Coupled Plasma Emission Spectrometry and Transmission Electron Microscopy equipped with EDS (Energy Dispersive Spectrometer). The glass phase content in Example 5 was 0.7 mol % of $Li_2O$ and 5.2 mol % of $SiO_2$ and the rest $Al_2O_3$, and the crystalline phase content in Example 5 consisted of 69 mol % of $Al_2O_3$, 4.9 mol % of $SnO_2$ and 19.7 mol % of $TiO_2$. The glass phase content in Example 6 was 1.0 mol % of $Li_2O$ and 7.7 mol % of $SiO_2$ and the rest $Al_2O_3$, and the crystalline phase content in Example 6 consisted of 65.2 mol % of $Al_2O_3$, 4.7 mol % of $SnO_2$ and 18.9 mol % of $TiO_2$. The glass phase contained in Example 7 was 1.9 mol % of $Li_2O$ and 13.9 mol % of $SiO_2$ and the rest $Al_2O_3$, and the crystalline phase content in Example 7 consisted of 57.6 mol % of $Al_2O_3$, 4.3 mol % of $SnO_2$ and 17.0 mol % of $TiO_2$. The glass phase contained in Example 8 was 3.1 mol % of $Li_2O$ and 23.2 mol % of $SiO_2$ and the rest $Al_2O_3$, and the crystalline phase content in Example 8 consisted of 47.9 mol % of $Al_2O_3$, 3.6 mol % of $SnO_2$ and 14.3 mol % of $TiO_2$. The glass phase contained in Example 9 was 5.2 mol % of $Li_2O$ and 38.8 mol % of $SiO_2$ and the rest $Al_2O_3$, and the crystalline phase content in Example 9 consisted of 33.5 mol % of $Al_2O_3$, 5.2 mol % of $SnO_2$ and 38.8 mol % of $TiO_2$. The glass phase contained in Example 10 was 5.6 mol % of $Li_2O$ and 41.9 mol % of $SiO_2$ and the rest $Al_2O_3$, and the crystalline phase content in Example 10 consisted of 37.6 mol % of $Al_2O_3$, 2.2 mol % of $SnO_2$ and 8.6 mol % of $TiO_2$.

In the case of Example 10 (Sample No. 14), the rate of change of impedance was not overly large. However, Example 10 may be unsuitable because the impedance itself of the humidity sensor is very high due to high glass phase content and may lead to inaccuracy in impedance/humidity conversion. From these data of Table 1, it is considered that a preferable content of the glass phase (amorphous phase) that covers grains of the crystalline phase is about 10 mol % to about 56 mol % of the humidity sensitive porous layer and the rest thereof constitutes crystalline phase grains.

EXPERIMENT EXAMPLE 3

Experiment Example 3 confirms the effect of temperature control on the heater.

Specifically, in a manner similar to that of Experiment Example 1, the humidity sensor of Example 1 was measured for humidity sensing characteristics (impedance) in the initial state and after the durability test using the shunt-type evaluation method specified in JIS Z 8806 (1981).

Figure 8:
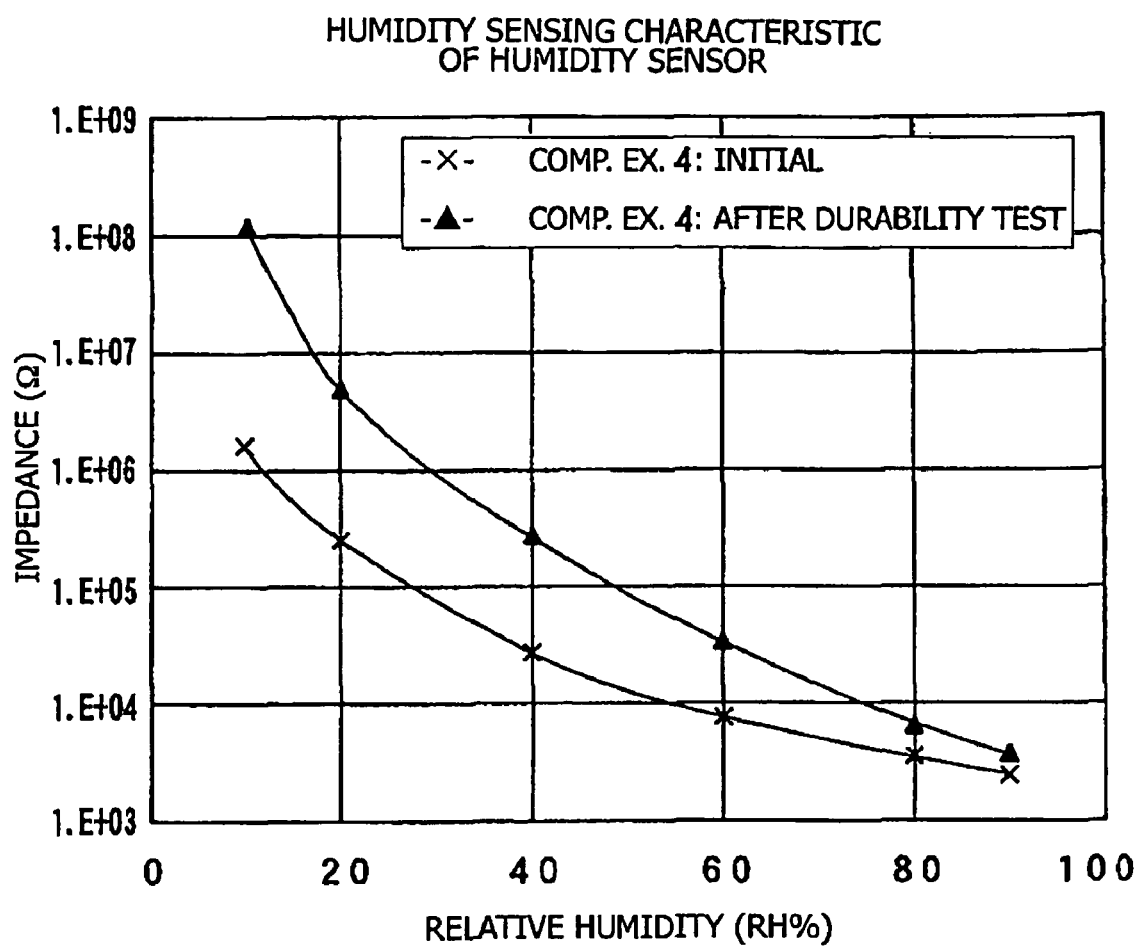
FIG. 8 is a graph showing humidity sensing characteristics of a humidity sensor of Comparative Example 4 in Experiment Example 3.
Figure 9:
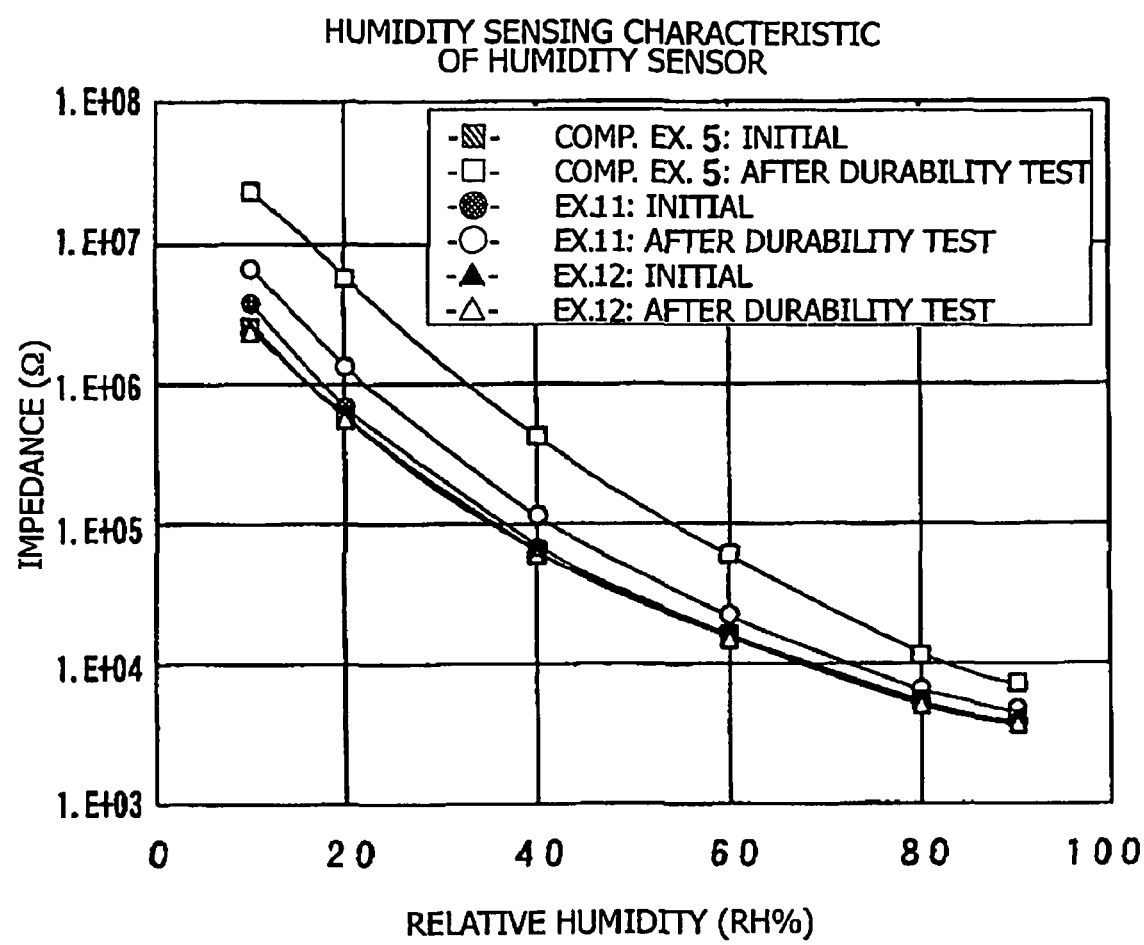
FIG. 9 is a graph showing humidity sensing characteristics of humidity sensors of Comparative Example 5 and Examples 11 and 12 in Experiment Example 3.
Figure 10:
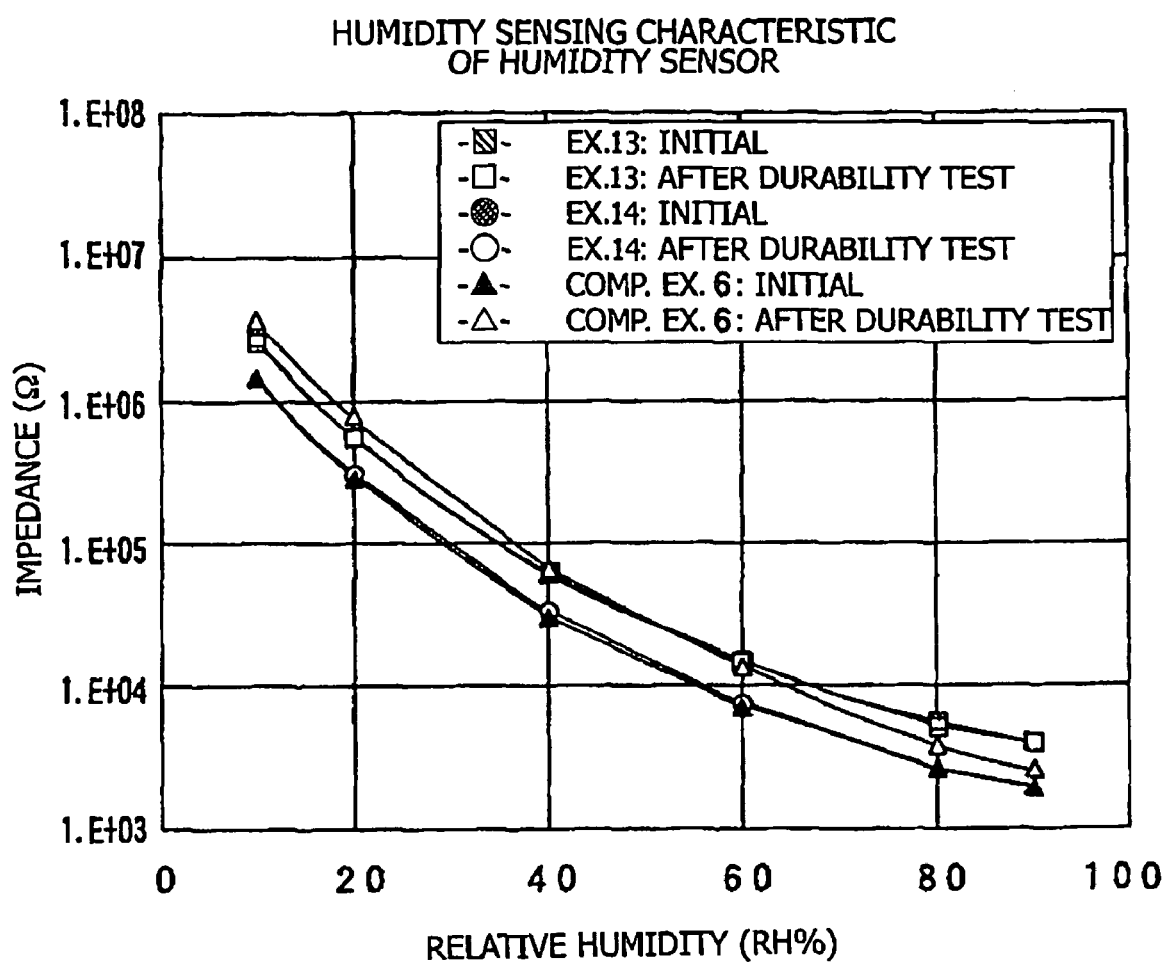
FIG. 10 is a graph showing humidity sensing characteristics of humidity sensors of Examples 13 and 14 and Comparative Example 6 in Experiment Example 3.

As shown below in Table 3, in Experiment Example 3, the heater control temperature was set to a temperature within 450° C. to 900° C. for the driving test. The test results are shown in FIGS. 8 to 10 (the vertical axis logarithmically represents impedance, and the horizontal axis represents relative humidity in RH %). Each of the sensors of Comparative Examples 4 to 6 and Examples 11 to 14 had the same composition and structure as the sensor of Example 1 of Experiment Example 1.

Notably, heat-applied cleaning in preparation for measurement was performed at 750° C. for 2 minutes. Measurement humidity was set to 10 RH %, 20 RH %, 40 RH %, 60 RH %, 80 RH %, and 90 RH %.

TABLE 3

| | Control | Heater Control Temp. [° C.] |
|---|---|---|
| Comparative Example 4 | No heater control | — |
| Comparative Example 5 | Heater control while running | 450 |
| Example 11 | Heater control while running | 500 |
| Example 12 | Heater control while running | 600 |
| Example 13 | Heater control while running | 700 |
| Example 14 | Heater control while running | 800 |
| Comparative Example 6 | Heater control while running | 900 |

FIG. 8 is a graph showing humidity sensing characteristics of the humidity sensor of Comparative Example 4, in which heater control was not performed, as measured in the initial state and after the durability test. As is apparent from FIG. 8, when heater control was not performed, impedance as measured at a humidity of 20 RH % after the durability test was about 18 times or more higher as compared with initial impedance, showing that the absence of heater control is unfavorable.

FIGS. 9 and 10 are graphs showing humidity sensing characteristics of the humidity sensors of Comparative Examples 5 and 6, in which heater control was performed, and humidity sensing characteristics of the humidity sensors of Examples 11 to 14 of the invention, as measured in the initial state and after the durability test.

In Comparative Example 5 shown in FIG. 9, heater control was performed at all times during the driving test such that a temperature sensor incorporated in the humidity sensor was held at a constant temperature of 450° C. As is apparent from FIG. 9, when heater control for heating at 450° C. was performed, impedance as measured at a humidity of 20 RH % after the durability test was about 10 times or more higher as compared with the initial impedance, indicating that such heater control is unfavorable.

By contrast, in Examples 11 to 14 shown in FIGS. 9 and 10, heater control was performed at all times during the driving test such that a temperature sensor incorporated in each of the humidity sensors was held at a constant temperature of 500° C. to 800° C. An excessive increase in impedance was not observed, indicating that such heater control is favorable and advantageous.

The present inventors consider that the above results are achieved because the glass phase is softened as a result of heating the humidity-sensitive layer by the heater for instance at the temperature of 750° C., thereby accelerating diffusion of the deposits into the glass phase of the humidity-sensitive porous layer and as a result, advantageously reducing adhesion of deposits onto the sensor at all times the internal combustion engine is running.

In Comparative Example 3 shown in FIG. 10, heater control was performed at all times during the driving test such that a temperature sensor incorporated in the humidity sensor was held at a constant temperature of 900° C. As is apparent from FIG. 10, when heater control for heating at 900° C. was performed, impedance as measured at a humidity of 20 RH % after the durability test was about 3 times or more higher as compared with the initial impedance. It is considered that the humidity-sensitive layer may be thermally deteriorated if heating the humidity sensitive element section at 900° C. is maintained for such a long time.

The above results indicate that when the heater is used to heat the humidity sensor element for further complete cleaning or rather refreshing, heating at a temperature higher than 800° C. should be restricted to a short period of time, and heating at a temperature beyond 1200° C. should be avoided due to softening of the glass phase. Further, the humidity sensitive porous layer is preferably heated at a temperature higher than 800° C. when the internal combustion engine is stopped, because there are no further deposits of fouling substances adhering onto the surface of the glass phase. This is because the engine is stopped and diffusion of such fouling substances into the glass phase can be limited or minimized. Duration of such heating in the temperature range of higher than 800° C. and up to 1200° C. should be less than 10 minutes, preferably a few minutes. At all times the internal engines is running, the heater is preferably controlled to heat the humidity sensitive element section at the temperature not exceeding 800° C., for instance, at the temperature of 750° C. After the engine is stopped, the heater is optionally controlled to heat the humidity sensitive cement section to the temperature higher than 800° C. for a short period of time for further cleaning off the element section and then the humidity measurement of the exhaust gas is carried out after the exhaust gas has cooled to a temperature not exceeding 100° C.

The above test results reveal that, by means of heating the humidity-sensitive layer having the glass phase covering the crystalline phase grains at a temperature ranging from 500° C. to 800° C. by the heater, variations in impedance of the humidity sensor installed for measurement of automotive exhaust gas can be advantageously suppressed over a long period of time.

As described above, in the present embodiment, the humidity sensor that includes the humidity-sensitive layer having the above-described structure is heated by use of the heater, and the heating temperature is controlled to a predetermined range. As a result, even when the humidity sensor is exposed to a very severe environment, such as an atmosphere within an automotive exhaust pipe, the humidity sensor can consistently exhibit excellent performance with high accuracy over a long period of time.

The present invention is not limited to the above-described embodiment, but may be embodied in various forms without departing from the scope of the invention.

(1) For example, the above embodiment performs feedback control on the heater. However, a constant voltage may be applied to the heater for a predetermined period of time or at a predetermined duty ratio (the period of time or the duty ratio is, for example, experimentally obtained such that the temperature of the humidity-sensitive element section does not increase excessively).

(2) The above embodiment performs feedback control on the heater on the basis of the resistance of the temperature sensor. However, feedback control may be performed on the heater on the basis of the resistance of the heater itself.

(3) The heater may be energized for heating at a temperature of 500° C. to 800° C. continuously or intermittently at all times so long as the engine is running and exhausting an exhaust gas having a temperature higher than 100° C. at which temperature the humidity measurement is not performed. Also, for example, after the internal combustion engine is stopped, the heater may be energized for heating at a temperature of 500° C. to 1,200° C. for a predetermined short period of time, and then, the humidity measurement may be carried out after the exhaust gas cools to a temperature below 100° C. The heating duration for cleaning the humidity sensitive element section depends on the heating temperature; the higher the temperature, the shorter the heating duration. A better analysis on a state of an internal combustion engine including an exhaust gas purifying apparatus may be attained if the humidity measurements are carried out each time after the engine is started and each time after the engine is stopped. The humidity sensor may be installed upstream and/or downstream of the exhaust gas purifying apparatus of the internal combustion engine for analysis on the exhaust gas exhausted therefrom.

(4) Heating temperature and time with respect to heating by the heater may be adjusted in accordance with a detection value indicative of the degree of fouling of the humidity sensor, such as impedance of the humidity sensor.

(5) Because the temperature of exhaust gas exhausted from an internal combustion engine varies depending on the operating condition of the internal combustion engine, the temperature of the humidity-sensitive element section also varies depending on an operating condition of the internal combustion engine. Thus, the duration of voltage application to the heater and applied voltage, for example, may be adjusted in accordance with an operating condition, such as intake pressure (negative pressure), vehicle speed, or engine speed.

This application is based on Japanese Patent Application No. 2003-155014 filed May 30, 2003, incorporated herein by reference in its entirety.

What is claimed is:

1. A humidity sensor for use in an exhaust gas purifying apparatus of an internal combustion engine, comprising:
   a humidity-sensitive element comprising a humidity-sensitive porous ceramic layer and detection electrodes formed on the humidity-sensitive porous ceramic layer; and
   a heater for heating the humidity-sensitive element at a temperature of from 500–1200° C.;
   wherein the humidity-sensitive porous ceramic layer comprises a crystalline phase formed of at least one oxide comprising crystalline oxide grains, and a glass phase,
   wherein the humidity sensitive porous ceramic layer has a skeletal structure formed of the crystalline phase and the glass phase, the glass phase covering the surface of individual crystalline oxide grains to form pores in the glass phase, and
   wherein the humidity-sensitive porous ceramic layer contains the glass phase in an amount of 10–56 mol %.

2. The humidity sensor as claimed in claim 1, wherein the detection electrodes contain platinum.

3. The humidity sensor as claimed in claim 1, wherein the glass phase comprises at least one selected from the group consisting of silicate glass, phosphate glass and borate glass.

4. The humidity sensor as claimed in claim 1, wherein the glass phase has a softening point of 800° C. to 1,200° C.

5. The humidity sensor as claimed in claim 1, comprising means for detecting, from humidity variation of exhaust gas, a condition or state of an exhaust-gas-purifying apparatus of an internal combustion engine.

6. The humidity sensor as claimed in claim 1, further comprising means for heating the humidity-sensitive element to a temperature higher than the cleaning temperature of 500° C. to 800° C. after the internal combustion engine is stopped.

7. The humidity sensor as claimed in claim 1, further comprising means for heating the humidity-sensitive element to a temperature higher than 800° C. but not exceeding 1200° C. after the internal combustion engine is stopped.

8. The humidity sensor as claimed in claim 1, further comprising means for heating the humidity-sensitive element to the cleaning temperature of 500° C. to 800° C. at all times while the internal combustion engine is running.

9. The humidity sensor as claimed in claim 1, comprising heater means for heating the humidity-sensitive element at a cleaning temperature of from 500° C. to 800° C. for a predetermined time while the internal combustion engine is running and exhausting an exhaust gas having a temperature exceeding 100° C. and for heating the humidity-sensitive element for a predetermined time to a temperature higher than 800° C. but not exceeding 1200° C. after the internal combustion engine is stopped, said humidity sensor measuring humidity of the exhaust gas after the internal combustion engine is started and while the exhaust gas temperature is not higher than 100° C., and/or said humidity sensor measuring humidity of the exhaust gas after the internal combustion engine is stopped and the exhaust gas has cooled to a temperature of not higher than 100° C.

10. The humidity sensor as claimed in claim 1, further comprising temperature detection means for detecting a temperature of the humidity-sensitive element and means for controlling the heater means such that the temperature detection means assumes a predetermined resistance.

11. The humidity sensor as claimed in claim 10, wherein said temperature detection means comprises a temperature sensor including a temperature sensitive resistor.

12. The humidity sensor as claimed in claim 10, wherein said temperature detection means comprises said heater means, said heater means having a resistance which varies with temperature.

13. The humidity sensor as claimed in claim 1, wherein said glass phase contains a glass component including an alkali metal oxide and/or an alkaline earth metal oxide in an amount of 0.5 mol % (namely 0.5% by mole) to 30 mol % of the glass phase.

14. The humidity sensor as claimed in claim 1, wherein said glass phase contains a glass component including an alkali metal oxide and/or an alkaline earth metal oxide.

15. The humidity sensor as claimed in claim 1, wherein the humidity-sensitive porous ceramic layer consists essentially of the crystalline phase formed of the at least one oxide, and the glass phase.

16. A method for measuring humidity of an exhaust gas exhausted from an internal combustion engine using a humidity sensor comprising, a humidity-sensitive element comprising a humidity-sensitive porous ceramic layer and detection electrodes formed on the humidity-sensitive porous ceramic layer; and
   a heater for heating the humidity-sensitive element at a temperature of from 500–1200° C.;
   wherein the humidity-sensitive porous ceramic layer comprises a crystalline phase formed of at least one oxide comprising crystalline oxide grains, and a glass phase,
   wherein the humidity sensitive porous ceramic layer has a skeletal structure formed of the crystalline phase and the glass phase, the glass phase covering the surface of individual crystalline oxide grains to form pores in the glass phase, and
   wherein the humidity-sensitive porous ceramic layer contains the glass phase in an amount of 10–56 mol %, said method comprises:
   heating the humidity-sensitive element with said heater to a cleaning temperature that removes fouling substances adhered on a surface of the humidity-sensitive porous ceramic layer, and
   measuring the humidity of exhaust gas having a temperature not higher than 100° C. based on impedance or resistance measured across the detection electrodes.

17. The method for measuring humidity as claimed in claim 16, wherein said cleaning temperature ranges from 500° C. to 800° C. when the internal combustion engine is running.

18. The method for measuring humidity as claimed in claim 16, wherein said cleaning temperature ranges from 500° C. to 1200° C. when the internal combustion engine is stopped.

19. The method for measuring humidity as claimed in claim 16, which comprises elevating said temperature beyond 800° C. up to 1200° C. with said heater after the internal combustion engine is stopped.

20. The method for measuring humidity as claimed in claimed in claim 16, which comprises (i) heating the humidity-sensitive element section with said heater to a cleaning temperature ranging from 500° C. to 800° C. so as to clean a surface of the humidity-sensitive porous ceramic layer while the internal combustion engine is running and exhausting an exhaust gas having a temperature exceeding 100° C., (ii) after the internal combustion engine is stopped, heating the humidity-sensitive element to a temperature higher than 800° C. but not exceeding 1200° C., and (iii) measuring humidity of the exhaust gas after the internal combustion engine is started and while the exhaust gas temperature is not higher than 100° C.

21. The method for measuring humidity as claimed in claim 16, wherein humidity measurement is carried out after the internal combustion engine is started and/or after the internal combustion engine is stopped.

22. The method for measuring humidity as clamed in claim 16, which comprises heating the humidity-sensitive element to a temperature higher than said cleaning temperature after the internal combustion engine is stopped.

23. The method for measuring humidity as claimed in claim 16, wherein the humidity-sensitive porous ceramic layer comprises a crystalline phase formed of an oxide, and a glass phase that contains an alkali metal oxide and/or an alkaline earth metal oxide, said humidity-sensitive porous ceramic layer containing the glass phase in an amount of 10 mol % to 56 mol % and said glass phase containing the alkali metal oxide and/or an alkaline earth metal oxide in an amount of 0.5 mol % (namely 0.5% by mole) to 30 mol % of the total glass phase.

24. The method for measuring humidity as claimed in claim 16, which comprises (i) heating the humidity-sensitive element with said heater to a cleaning temperature ranging from 500° C. to 800° C. so as to clean a surface of the humidity-sensitive porous ceramic layer while the internal combustion engine is running and exhausting an exhaust gas having a temperature exceeding 100° C., (ii) after the internal combustion engine is stopped, heating the humidity-sensitive element to a temperature higher than 500° C. but not exceeding 1200° C., and (iii) measuring humidity of the exhaust gas while the exhaust gas temperature is not higher than 100° C.

25. The method for measuring humidity as claimed in as claimed in claim 16, comprising heating the humidity-sensitive element to the cleaning temperature of 500° C. to 800° C. at all times while the internal combustion engine is running.

26. The method for measuring humidity as claimed in 25, further comprising heating the humidity-sensitive element to a temperature of 500° C. to 1200° C. when or after the engine is stopped.

27. The method for measuring humidity as claimed in claim 21, comprising measuring humidity of the exhaust gas when the exhaust gas shows a temperature of not higher than 100° C.

28. The method for measuring humidity as claimed in claim 16, wherein the humidity measurement is carried out only when the temperature of the exhaust gas is not higher than 100° C.

* * * * *